United States Patent [19]

Howell et al.

[11] Patent Number: 5,409,690
[45] Date of Patent: Apr. 25, 1995

[54] TREATMENT OF MULTIDRUG RESISTANT DISEASES IN CANCER CELL BY POTENTIATING WITH MASOPROCOL

[75] Inventors: Stephen Howell, Del Mar, Calif.; Atul Khandwala, Edgewater, N.J.; Om P. Sachdev, New City, N.Y.; Charles G. Smith, Rancho Santa Fe, Calif.

[73] Assignee: Chemex Pharmaceuticals, Inc., Fort Lee, N.J.

[21] Appl. No.: 81,663

[22] Filed: Jun. 23, 1993

[51] Int. Cl.⁶ ............... A61K 48/00; A61K 31/70; A61K 31/045
[52] U.S. Cl. ........................ 424/10; 514/34; 514/727; 514/731
[58] Field of Search ............... 514/34, 727, 731; 424/10

[56] References Cited

U.S. PATENT DOCUMENTS 5,008,294  4/1991  Jordan et al. ............... 514/731

OTHER PUBLICATIONS

Carter et al; Chemotherapy of Cancer, Second Edition, A Wiley Medical Publication, 1981 pp. 361-365.

*Primary Examiner*—Raymond Henley, III
*Assistant Examiner*—T. J. Criares
*Attorney, Agent, or Firm*—Weiser & Associates

[57] ABSTRACT

Disclosed are: a method for reversing multidrug resistance in a mammal; and a composition to reverse multidrug resistance comprising:

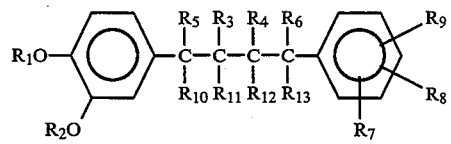

wherein
$R_1$ and $R_2$ are independently H, lower alkyl or lower acyl;
$R_3$, $R_4$ and $R_5$ are independently H or lower alkyl;
$R_7$, $R_8$ and $R_9$ are independently H, hydroxy, lower alkoxy or lower acyloxy; and
$R_{10}$, $R_{11}$, $R_{12}$ and $R_{13}$ are independently H or lower alkyl, in a pharmaceutically acceptable vehicle.

22 Claims, No Drawings

TREATMENT OF MULTIDRUG RESISTANT DISEASES IN CANCER CELL BY POTENTIATING WITH MASOPROCOL

BACKGROUND OF THE INVENTION

Field of the Invention

This invention relates to a method of preventing development of multidrug resistance (hereinafter MDR) and to a method of reversing MDR if one already exists thereby to prevent or correct drug accumulation defect in drug resistant cells. More particularly, the invention relates to the administration of masoprocol along with antineoplastic/cytotoxic drugs to which cells develop multidrug resistance (MDR), e.g. Doxorubicin, Daunorubicin, Amsacrine Mitoxantrone, Dactinomycin, Ellipticine, Etoposide, Teniposide, Chlorambucil, Melphalan, Cyclophosphamide, Nitrosoureas BCNU, CCNU, MeCCNU), Methotrexate, Trimetrexate, 5-FU, Ara-C, Ara-A, Cisplatin, Carboplatin and Taxol.

Reported Developments

Patients having solid malignant tumors e.g., breast, ovarian, lung, colon and hematological malignant disorders, such as refractory myeloma, often develop MDR .... MDR is associated with the overexpression of an MDR-1 gene that codes for a plasma membrane P-glycoprotein. The expression of the MDR-1 gene is believed to be associated with a decreased cellular accumulation of drug due to an active energy dependent efflux mechanism. The active efflux of drug is believed to be mediated by the P-glycoprotein efflux pump.

Attempts have been made to reverse MDR and to correct the drug accumulation defect in drug resistant cells. Among the agents which show promise in vitro are verapamil, quinidine, amioderone, cyclosporin and certain phenothiazines. It appears, however, that in vivo concentrations necessary to reverse MDR cannot be achieved without substantial toxicity to patients.

SUMMARY OF THE INVENTION

Masoprocol is new MDR modulating agent. We have discovered that the combination of masoprocol known as nordihydroguaiaretic acid (hereinafter sometimes referred to as NDGA) or certain analogues thereof in combination with cytotoxic agents, e.g. Doxorubicin, Daunorubicin, Amsacrine, Mitoxantrone, Dactinomycin, Ellipticine, Etoposide, Teniposide, Chlorambucil, Melphalan, Cyclophosphamide, Nitrosoureas (BCNU, CCNU, MeCCNU), Methotrexate, Trimetrexate, 5-FU, Ara-C, Ara-A, Cisplatin, Carboplatin and Taxol can overcome multidrug resistance of certain diseased cells and has the potential of being effective in the treatment of solid malignant tumors e.g., brain, breast, colon, lung, ovarian cancers and hematological malignant disorders including lymphoma, leukemia (acute nonlymphocytic leukemia, acute myelocytic leukemia), or increase the therapeutic effectiveness of the above-mentioned cytotoxic agents.

The naturally occurring meso form of the nordihydroguaiaretic acid [meso- 1,4-bis (3,4-dihydroxyphenyl)-2,3-dimethylbutane] ("NDGA") was reported as providing a positive result against malignant melanoma. C. R. Smart, et al, *Rocky Mountain Medical Journal*, November 1970, pp. 39-43. (Unless otherwise indicated, NDGA is used herein to refer to the meso form of nordihydroguaiaretic acid). NDGA is found in the creosote bush, and this plant was used for centuries to brew tea which was the basis for a folk remedy that called for drinking the tea to cure colds, rheumatism and other ailments. However, this remedy has not proven to be successful.

A clinical study was conducted by Smart et al, reported in U.S. Pat. No. 4,880,637, in which human cancer patients ingested either a tea made form the creosote bush or doses of pure NDGA. This study indicated that neither NDGA nor the tea were effective anticancer agents and in some cases caused stimulation of tumor cell growth. This confirmed the earlier screening studies of NDGA conducted by Leiter et al of the Cancer Chemotherapy National Service Center of National Cancer Institute which obtained negative results when NDGA was tested against several types of cancer cells.

It has been reported in U.S. Pat. No. 4,880,637 that NDGA and its analogues in combination with ionic zinc is effective in the treatment of benign, paramalignant and malignant growth of the skin without detrimental side effects associated with chemotherapy or chemosurgical techniques.

NDGA was also reported in U.S. Pat. No. 4,695,590, as having efficacy in retarding senescence or aging in mammals.

To our knowledge, NDGA in combination with other cytotoxic/antineoplastic chemotherapeutic drugs is not known, nor have been reported to inhibit multidrug resistance associated with the treatment of solid malignant tumors or hematological disorders in mammals.

In the modern clinical oncology practice, it has been established that overexpression of P-glycoprotein (Pgp) in cancer patients is directly related to the increase in the multidrug resistance (MDR) to treatment with presently available chemotherapies. The present inventors have discovered that masoprocol (NDGA) overcomes the Pgp mediated resistance and Pgp antagonism of the cells, thereby increasing the levels of chemotherapeutic drugs which accumulate in the cancer cells.

The present invention provides a method and composition for the inhibition and/or reversal of multidrug resistant phenomenon in a patient and thereby treatment of solid malignant tumors and hematological malignancies comprising the administration of NDGA to said patient preferably in a pharmaceutically acceptable vehicle.

The general formula comprises of from about 0.1% to about 25% NDGA or an analogue thereof in a pharmaceutically acceptable vehicle for topical application or of from about 1 mg NDGA to about 500 mg of NDGA per kg of body weight for systemic administration.

NDGA and its analogues used in the present invention have the following Formula (I):

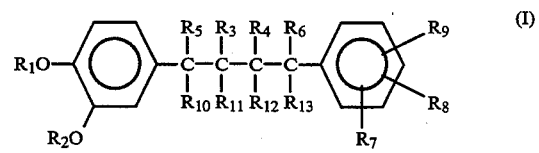

wherein
  $R_1$ and $R_2$ are independently H, lower alkyl or lower acyl;
  $R_3$, $R_4$, $R_5$, and $R_6$ are independently H or lower alkyl; $R_7$, $R_8$ and $R_9$ are independently H, hydroxy, lower alkoxy or lower acyloxy; and $R_{10}$, $R_{11}$, $R_{12}$ and $R_{13}$ are independently H or lower alkyl.

Lower alkyl is intended to generally mean $C_1$-$C_6$ alkyl, and preferably $R_3$ and $R_4$ are $C_1$-$C_3$ alkyl. Lower acyl is intended to generally mean $C_1$-$C_6$ acyl, with $C_2$-$C_6$ acyl being preferred. The formula is directed to both the phenolic compounds and the conventional esters and ethers thereof.

DETAILED DESCRIPTION OF THE INVENTION

NDGA and its analogues (also referred to herein as catecholic butanes) according to the present invention, may be made by the synthetic methods provided in U.S. Pat. Nos. 4,562,298 and 4,954,659 which are incorporated herein by reference in their entirety.

Examples of catecholic butanes include: the d-, l-racemic mixture of d- and l-, meso-isomers of 1,4-bis(3,4-dihydroxyphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3',4',5'-trihydroxyphenyl)butane; 1,4-bis(3,4-diacetoxyphenyl)-2,3-dimethylbutane; 1,4-bis(3,4-dipropionyloxyphenyl)2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; 1-(3,4-dihydroxyphenyl)-4-phenylbutane and 1-(3,4-dihydroxyphenyl-4-(2,5dihydroxyphenyl)butane. Mixtures of Formula (I) may be used in the instant composition as well.

The compositions of the present invention are believed to be effective in the treatment of solid mammalian tumors or hematologic malignancies which can develop multidrug resistance. These solid tumors include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin, central nervous system; sarcomas of the soft tissue and bone; and melanomas of cutaneous and intraocular origin. Itematological malignancies include childhood leukemias and lymphomas, Hodkin's disease, lymphomas of lymphocytic and cutaneous origin, acute and chronic leukemia, plasma cell neoplasm and cancers in AIDS. The preferred mammalial species to be subjected to the present invention are humans and domesticated animals.

The instant compositions can be applied topically, orally or parentially to the treatment site. When used for topical application, NDGA is usually formulated with a pharmaceutically acceptable carrier. Carrier materials are well known in the pharmaceutical formulation art and include those materials referred to as diluents or vehicles. The carrier may include inorganic or organic materials and should have sufficient viscosity to allow spreading of the composition and provide good adherence to the tissue to which it is topically applied. Examples of such carriers include, without limitation, polyols such as glycerol, propylene glycol, polyethylene glycol, preferably of a molecular weight between about 400 to about 8000, suitable mixtures thereof, vegetable oils, and other materials well known to those skilled in this art. The viscosity of the formulation can be adjusted by methods well known in the art, for example, by the use of a higher molecular weight polyethylene glycol.

In addition to NDGA, the formulation can contain pharmacologically-acceptable additives or adjuvants such as antimicrobial agents, e.g. methyl, ethyl, propyl and butyl esters of parahydroxybenzoic acid as well as chlorobutanol, phenol, ascorbic acid, etc. The formulation can also contain thickening or gelling agents, emulsifiers, wetting agents, coloring agents, buffers, stabilizers and preservatives including antioxidants such as butylhydroxyanisole in accordance with the practice of the art. The formulation can also contain penetration enhancers such as dimethylsulfoxide, long-chain alcohols such as nonoxynol, long-chain carboxylic acids, propylene glycol, N-(2-hydroxyethyl)pyrrolidone, 1-dodecyl-azacycloheptan-2-one, and the like. Depending on the method of application and the disease being treated, it may be desirable to use absorption-delaying agents such as aluminum monostearate and gelatin.

The compositions of the formulation can be adjusted using components well-known in the formulation art to provide a pharmaceutical formulation which is a gel, cream, ointment, solid, liquid, semi-solid, etc. The particular physical form of the formulation depends on the desired method of treatment and the patient to be treated.

For administration by injection, the compositions according to the invention are formulated as solutions or suspensions having a low enough viscosity to be injected. The composition suitable for injectable use must be sterile and fluid to the extent that easy syringe injection exists. It should also be stable under conditions of manufacturer and storage and be preserved against contamination by microorganisms. Preservatives include alcohol, benzoic acid, sorbic acid, and methyl and propyl parabin with and without propylene glycol. Additionally, the pH of the composition must be within a range which does not result in tissue damage, namely, between about 3.0-7.5.

The concentration of NDGA in a particular formulation depends on the condition being treated, the method of application, i.e. topical or injection, the rate of delivery of the active ingredient(s) to the treatment site, and the number of applications of the formulation which can be used. Additionally, certain NDGA analogues are more effective in treating particular conditions that are other analogues. The concentration of verapamil in the formulation likewise depends upon the condition being treated and the particular NDGA analogue or combination of analogues being used.

The pH of the formulation is important in assuring stability of NDGA or its analogue as well as assuring that the formulation is physiologically acceptable to the patient. Many of the analogues, and particularly nordihydroguaiaretic acid, are susceptible to oxidation, for example, by air. Such oxidation can result in discoloration of the formulation rendering it unacceptable for pharmaceutical use. These catechols are more stable against oxidation at lower pH levels. Therefore, it is preferred that if the formulation is to be exposed to oxidizing conditions the pH to be maintained below about 7 and preferably below about 6 in order to provide maximum stability for the compound against oxidation. However, if the oxidizing conditions can be avoided, for example, by storage of the formulation under an inert atmosphere such as nitrogen, a higher pH can be used. The pH of the formulation may be maintained through the use of toxicologically-acceptable buffers. Such buffers are well-known in the pharmaceutical formulation art, and include hydrochloric acid buffer, acid phthalate buffer, phosphate buffer and citric acid/sodium citrate buffer.

The following example will further illustrate the formulations of the present invention.

| Active Ingredient | |
|---|---|
| NDGA | 10 |
| Excipients, Purified water USP | 48.25 |
| Propylene glycol USP | 12.0 |
| Polyethylene glycol 400 NF | 7.5 |
| Stearyl alcohol NF | 5.0 |
| Light mineral oil NF | 5.0 |
| Synthetic beeswax | 3.5 |
| Isostearyl alcohol | 3.0 |
| Steareth-2 | 2.75 |
| Steareth-21 | 2.25 |
| Xanthum gum NF | 0.40 |
| Methylparaben, NF | 0.16 |
| Sodium bisulfite | 0.10 |
| Propylparaben NF | 0.08 |
| Citric acid USP | 0.01 |

For systemic administration, NDGA or analogues can be given as a suspension in methocel, buffered saline, i.v. as a sterile injectable and orally as a tablet or a capsule.

The tests were performed to determine the effect of NDGA on efflux of doxorubicin (hereinafter sometimes referred to as DOX) for doxorubicin sensitive MCF7/0 and doxorubicin resistant MCF7/ADR human breast adenocarcinoma cells in vitro.

The cells were exposed to 50 μg/ml NDGA for 24 hrs prior to loading with DOX (doxorubicin) at 37° C. Each cell line was loaded with DOX (5 μg×30 min) and selected samples were treated with verapamil (30 μl of a 1 mM solution) at the end of the loading period and then pelleted and suspended in 37° C. PBS. Flow analysis of cell efflux of DOX was collected over 30 minutes using the time parameter. The results are shown in Table I.

retention in both NDGA and NDGA+verapamil. The results indicate NDGA will inhibit the efflux of DOX via the p170 (p-glycoprotein) resistance factor. 3) Treatment of multidrug resistant MCF7/ADR and its parent cell line MCF7/0, human breast adenocarcinoma cells line with 50 μg/ml in clonogenic assay resulted in an increased doxorubicin accumulation of 25.6% and 44.5% respectively. In comparison experiment of same cell lines with verapamil treatment resulted in a 36% increased accumulation in the doxorubicin resistant cells (i.e. MCF7/ADR) and no increase accumulation of doxorubicin concentration in the parent MCF7/0 cells.

We conclude that NDGA is a novel agent capable of reversing MDR and potentiation of chemotherapeutic activity of doxorubicin in vitro and its usage as reversing the multidrug resistance in solid malignant tumors and hematological malignancies.

Procedure for P-Glycoprotein (PGP) Function Assay of Doxorubicin Efflux is shown hereunder.
1. Verapamil (GFW=491.1) Make a 1 mM solution by dissolving 4.911 mg of Verapamil per 10 mls of distilled water. Store at room temperature.
2. Doxorubicin (GFW=580) Make a solution of doxorubicin to contain 10 μg/ml. Store frozen at 0° C.
3. Rhodamine 123 (GFW=380.0) Make a 1 mM solution by dissolving 3.808 mg per mls of absolute ethanol. Store at −20° C.
4. NDGA (MW=302.36) Make a solution of NDGA to contain 50 μg/ml. Store frozen at 0° C.
5. MCF7/0 (Doxorubicin sensitive) and MCF7/ADR (Doxorubicin resistant), human breast adenocarcinoma cell lines.

Procedure

1. Make up $2\times10^6$ cells per ml in PBS. Expose 1 ml of cells to 50 μg of NDGA for 24 hrs at 37° C. prior to loading with Doxorubicin.
2. Add 1 ml of 10 μg/ml doxorubicin, mix and divide into two aliquots.
3. Add 30 μl of verapamil to one aliquot.

TABLE I

THE EFFECT OF NDGA ON STEADY STATE ACCUMULATION OF DOX IN MCF7/0 AND MCF7/ADR CELLS LINES

| | TREATMENT | CHANNEL FLUORESCENCE | % DOX INCREASE w/VERAPAMIL | % DOX INCREASE w/NDGA |
|---|---|---|---|---|
| MCF7/0 | | | | |
| No NDGA | DOX | 318.7 | — | — |
| | DOX + Verapamil | 312.8 | 0.981 | — |
| RX NDGA | DOX | 460.4 | — | 44.5 |
| | DOX + Verapamil | 435.6 | 0.946 | — |
| MCF7/ADR | | | | |
| No NDGA | DOX | 227.4 | — | — |
| | DOX + Verapamil | 309.9 | 36.3 | — |
| RX NDGA | DOX | 285.6 | — | 25.6 |
| | DOX + Verapamil | 365.4 | 27.9 | — |

DOX = Doxorubicin

In the table, the loading of DOX in cells (Mean Channel Fluorescence) and the % value represent the increase of DOX measured in the cells after treatment with verapamil or NDGA.

Two interesting results are seen with this experiment: 1) the MCF7 cells (sensitive) are loading more DOX after NDGA treatment than controls or verapamil treated cells. This is of interest because verapamil has no effect on sensitive cells. 2) In the resistant MCF7/ADR cells there is an augmentation of DOX 4. Incubate both tubes at 37° C. for 30 minutes. P-glycoprotein function is temperature dependent, so do not place tubes on ice afterwards.
5. Centrifuge the tubes at 37° C. for 5 minutes on a fast spin to pellet cells. Resuspend in 1 ml of buffer.
6. Run immediately on the flow cytometer. Excitation 488 nm, emission 560–600 nm. Collect forward and 90° side scatter and PMT4 linear scale. Collect 10,000–50,000 events and calculate the mean channel fluorescence (MCF) for PMT4.

7. Run both samples as close together as possible, and avoid prolonged exposure to room temperature.

Calculations

1. Express results as percent increase in mean doxorubicin fluorescence in the verapamil-containing sample.

$$\% \ DOX \ increase = \frac{MCF \ DOX/Verapamil - MCF \ DOX \times 100}{MCF \ DOX}$$

Procedural Notes

1. If rhodamine 123 is used in the place of doxorubicin ad fluorescent stain, suspend $2 \times 10^6$ viable cells in 2 mls of PBS, add 10 $\mu$l of rhodamine to the cells, mix, and divide into two equal aliquots. Add verapamil to one tube and incubate as above. Collect green (PMT2) fluorescence.

2. Keep cells at 37° C. Avoid prolonged exposure to room temperature and do not place cells on ice at any step of the procedure.

Table II shows anti-tumor activity of NDGA against various tumor cell lines.

TABLE II

MASOPROCOL - (NDGA) IN VITRO (CYTOTOXICITY) ANTI TUMOR ACTIVITY

| | IC$_{50}$($\mu$M) | | | |
|---|---|---|---|---|
| | One Hour Pulse Treatment | | *Continuous Drug Exposure | |
| Tumor Cell Line | Masoprocol | Doxo-rubicin | Masoprocol | Doxo-rubicin |
| CAK-1 Renal | 211 | 3.8 | 53.4 | 0.11 |
| DLD-1 Colon | 124 | 3.7 | 0.08 | 0.42 |
| Lung (NCI-H23) | 172 | 9.3 | 0.08 | 0.15 |
| Lung (LX- 1) Chemex | 18 | 26 | | |
| LOX-IMVI Melanoma | 38.4 | 4.8 | 0.08 | 0.09 |
| SNB Glioblastoma | 312 | 0.7 | 0.08 | 0.03 |
| OVCAR3 Ovarian | 258 | 13.8 | 35.9 | 0.7 |
| WI-38 Lung Fibroblasts | 159 | 10.0 | 312 | 0.6 |
| Detroit 551 Skin Fibroblasts | 62.7 | 3.2 | 312 | 5.5 |
| Hs 68 Newborn Foreskin Fibroblasts | 178 | 11.6 | 18 | 0.12 |

*Drug Treatment with observation at 70 hours

As various changes might be made in the formulations of the invention herein disclosed, without departing from the spirit and principles of the invention, it is understood that all matter herein described shall be deemed illustrative, and not limiting except as set forth in the appended claims.

What is claimed is:

1. A method for treating cancer cells in a patient which cells are susceptible to multidrug resistance or cells which have become multiple drug resistant which comprises administering to said patient an effective amount of masoprocol and an effective amount of doxorubicin (DOX), whereby the masoprocol increases the therapeutic effect of doxorubicin.

2. The method of claim 1 wherein the cells are multidrug resistant.

3. The method of claim 1 wherein the cells are multidrug susceptible.

4. The method of claim 1 wherein the cells are exposed to NDGA followed by loading with DOX.

5. The method of claim 2 which comprises further treating the multidrug resistant cells by administration of verapamil.

6. The method of claim 2 wherein the cancer tumors are selected from the group selected of renal, colon, lung, melanoma, glioblastoma, ovarian, fibroblast, and human breast adenocarcinoma cells.

7. The method of claim 6 wherein the cancer cells are selected from the following CAK-1 renal, DLD-1 colon, lung (NCI-H23), lung (LX-1), LOX-IMVI melanoma, SNB glioblastoma, OVCAR3 ovarian, WI-38 lung fibroblast, Detroit 551 skin fibroblasts, Hs 68 newborn foreskin fibroblasts, MCF7/0 human breast adenocarcinoma, and MCF7/ADR human breast adenocarcinoma.

8. The method of claim 1 wherein the cancer cells have developed resistance to DOX.

9. The method of claim 1 wherein the treatment with NDGA increases the accumulation of DOX in cancer cell.

10. The method claim 1 wherein the administration is with a pharmaceutical composition which comprises masoprocol and a pharmaceutical composition which compresses doxorubicin, each composition including a pharmaceutically acceptable vehicle.

11. The method of claim 10 wherein the treatment is with the pharmaceutical composition is a topical treatment.

12. The method of claim 11 wherein the pharmaceutical composition for the topical treatment is in the form of an emollient.

13. The method of claim 11 wherein the pharmaceutical composition for the topical treatment is in the form of a cream.

14. The method of claim 11 wherein the pharmaceutical composition for the topical treatment is in the form of an ointment.

15. The method of claim 11 wherein the pharmaceutical composition for the topical treatment is in the form of a liposomal preparation.

16. The method of claim 11 wherein the pharmaceutical composition for the topical treatment is in the form of a membrane patch.

17. The method of claim 11 wherein the pharmaceutical composition which is a solid composition.

18. The method of claim 13 wherein the pharmaceutical composition which is a liquid composition.

19. The method of claim 10 wherein the pharmaceutical composition which is an injectable composition.

20. The method of claim 10 wherein the pharmaceutical composition has a pH in the range of 3.0 to 7.5.

21. The method of claim 20 wherein the pharmaceutical composition has a pH in the range from 6 to 7.

22. The method of claim 10 wherein the administration of the respective compositions is sequential.

* * * * *